United States Patent [19]

Brosnan et al.

[11] Patent Number: 4,987,086

[45] Date of Patent: Jan. 22, 1991

[54] METHOD FOR ANALYSIS OF SUBPOPULATIONS OF CELLS

[75] Inventors: Jeanne M. Brosnan, Stanford, Calif.; Kenneth A. Ault, Brunswick, Me.

[73] Assignee: Becton, Dickinson and Company, Franklin Lakes, N.J.

[21] Appl. No.: 126,333

[22] Filed: Nov. 30, 1987

[51] Int. Cl.$^5$ .................. C12Q 1/00; G01N 33/53; G01N 33/80; G01N 33/533

[52] U.S. Cl. .................. 436/501; 356/39; 435/2; 435/4; 435/7.24; 436/56; 436/805; 436/808

[58] Field of Search ............. 436/56, 501, 546, 805, 436/808; 422/44; 435/2, 4, 7, 808; 356/73, 39

[56] References Cited

U.S. PATENT DOCUMENTS

| | | | |
|---|---|---|---|
| 3,826,647 | 7/1974 | Bomner et al. | 209/3 |
| 4,284,412 | 8/1981 | Hansen et al. | 436/805 |
| 4,294,817 | 10/1981 | Burgett et al. | 435/4 |
| 4,381,292 | 4/1983 | Bieber et al. | 435/2 |
| 4,520,110 | 5/1985 | Stryer et al. | 436/501 |
| 4,596,035 | 6/1986 | Gershman et al. | 382/6 |
| 4,599,304 | 7/1986 | Lanier et al. | 435/4 |
| 4,599,307 | 7/1986 | Saunders et al. | 436/519 |
| 4,607,007 | 8/1986 | Lanier et al. | 435/7 |
| 4,657,852 | 4/1987 | Grumet et al. | 435/7 |
| 4,677,056 | 6/1987 | Dupont et al. | 435/7 |
| 4,727,020 | 2/1988 | Recktenwald | 435/6 |
| 4,767,206 | 8/1988 | Schwarz | 356/73 |
| 4,810,487 | 3/1989 | Kass | 436/805 |
| 4,824,775 | 4/1989 | Dattagupta et al. | 435/7 |

OTHER PUBLICATIONS

Simultest LeucoGATE Product Brochure.

Primary Examiner—Robert J. Warden
Assistant Examiner—Kimberly A. Trautman
Attorney, Agent, or Firm—Robert M. Hallenbeck

[57] ABSTRACT

A method and kit for determination of subsets of leukocytes utilizing flow cytometry analysis techniques.

25 Claims, 7 Drawing Sheets

METHOD FOR ANALYSIS OF SUBPOPULATIONS OF CELLS

FIELD OF THE INVENTION

The present invention relates to a method and apparatus for distinguishing and identifying subpopulations of cells in a blood sample, and more particularly, relates to a method and apparatus for distinguishing and quantifying subpopulations of lymphocytes in a sample through use of flow cytometry by gating on data retained from a prior sample.

DESCRIPTION OF THE PRIOR ART

Presently known and available flow cytometers useful for detecting particles, cells and the like, commonly include one or more, usually two, fluorescent channels for the detection of one or more subpopulations of cells in a mixture. The flow cytometer also usually includes means for determining cell volume, forward light scatter and/or side light scatter. The fluorescence channels are used to distinguish cells labeled with distinct fluorochromes which can be excited to emit light at different wave lengths. Cell volume, forward light scatter and side light scatter measurements are used to separate classes of cells based upon physical parameters.

For example, flow cytometry devices are known which include two fluorescence detectors which can detect cells specifically labeled with two immunofluorescent agents associated with the respective fluorescence detectors. In these known devices, a complete fluorescence detector, including the electrical circuitry and photo multiplier tube, is used for each type of fluorochrome labeled cells to be detected in the mixture of cells in the sample being analyzed. Therefore, to detect multiple subpopulations of cells in a sample using flow cytometry, an equivalent number of fluorescence detectors to fluorochromes is used. The cell volume, forward light scatter and side light scatter properties are also used to distinguish cells on the basis of physical parameters. Information can be obtained using a single pass of the cells through the flow cytometer and collecting data provided by the detection of separate fluorescence signals and physical parameters.

In the field of hematology in general, and in the specific field of immunonematology, it is desirable to determine the count of a variety of white blood cells (leukocytes) which circulate in the peripheral blood. Subclassification of cells is performed and the count of cells in the subpopulations is of great interest in the evaluation of immune related diseases, such as acquired immune deficiency syndrome (AIDS). In particular, the subpopulations of the lymphocytes, a mononuclear type of leukocytes, has become of great clinical significance.

For example, it may be desirable to detect or quantify the total population of lymphocyte cells in the blood sample and to determine the proportion of T-cells and B-cells as a percentage of the lymphocyte population. Similarly, the detection and quantification of other types of lymphocytes, such as the helper/inducer cell subset of T-cells and the suppressor/cytotoxic subset of T-cells may be desired.

In performing an analysis on a sample of blood which includes all of the leukocytes, it is common for flow cytometry operators to estimate the best gate that can be set which surrounds the population of lymphocytes. To establish this best gate by visual observation, a sample of the blood containing the leukocytes is passed through the flow cytometer and the operator observes the results on an oscilloscope using forward light scatter (or cell volume) and side light scatter. By manipulating the controls of the flow cytometer (or data retention device) the operator can select (by drawing) a gate which will exclude cells which are not within the gate and will only retain information generated by cells which are within the gate. Typically, this is done by means of a "curser" whose movement is tied into the data retention device (i.e., computer). The curser is moved to create the gate around the lymphocyte or other cell population of interest by tracing or circumscribing a line. Such establishment of a gate by visual observation is open to substantial error and substantial differences of observation between different operators.

With this in mind, the present invention is directed to satisfying a desired need for the direct determination of subpopulations of cells, and especially lymphocytes from a blood sample, including substantially all of the leukocytes, by automatically establishing a cell population gate without the need for manipulation of the flow cytometer by an operator.

It is, accordingly, the primary object of the present invention to provide a method for identifying and enumerating subpopulations of leukocytes while avoiding the necessity for the operator to visually select a gate by observation of the passage of cells in a sample through a flow cytometer. It is another object of the invention to provide a method for analysis of leukocytes so as to distinguish and quantify populations of leukocytes which substantially prevents faulty analysis due to operator error. It is a further object to provide a method for analysis of subpopulations of lymphocytes wherein the speed and relative simplicity involved renders lymphocyte subpopulation identification and enumeration a viable clinical tool.

SUMMARY OF THE INVENTION

The present invention is directed to a method and apparatus for determination of subsets of leukocytes utilizing flow cytometry analysis techniques. In accordance with one embodiment of the method for identifying subpopulations of lymphocytes in a blood sample, a first aliquot of a blood sample is provided which includes substantially all of the leukocytes. A first monoclonal antibody is labeled with a first fluorochrome. The first monoclonal antibody reacts with substantially all the leukocytes in the sample. A second monoclonal antibody is labeled with a second fluorochrome. The second monoclonal antibody reacts with substantially all of the monocytes in the sample. The first fluorochrome and the second fluorochrome have emission spectra which are different.

A mixture of the first aliquot, the first labeled monoclonal antibody and the second labeled monoclonal antibody then is prepared so as to cause the leukocytes to become labeled with the first monoclonal antibody and the monocytes to become labeled with the second monoclonal antibody. The first aliquot is then analyzed by flow cytometry so as to distinguish the lymphocyte population of the leukocytes. In the preferred embodiment, data for each of the four parameters (i.e., forward light scatter, side light scatter and fluorescence excitation energy) is collected for each cell as it passes through the flow cytometer. The data for each cell in the first aliquot is stored in the data retention device, and then is used to distinguish cell populations. Alternatively, cell volume may be used in place of forward light scatter.

A second aliquot of the blood sample then is provided from which it is desired to set a fluorescence markers and determine the percentage of cells which are non-specifically stained. Fluorescence markers are the boundaries which delineate positive from negative fluorescence events for each fluorochrome— and —from the first aliquot. The percentage of non-specific staining is the percent of gated events for each fluorochrome— and —from the first aliquot that fall in the positive fluorescence regions for this sample.

The second aliquot can be unlabeled or labeled with irrelevant monoclonal antibodies which are not reactive with any leukocytes (e.g., $IgG_1$, $IgG_2$ isotype monoclonals) to establish the fluorescence markers. Preferably, the second aliquot is labeled and is then analyzed by flow cytometry using forward light scatter, side light scatter and fluorescent excitation energy. The gate from the first aliquot then is applied. Thus, only cells having scatter characteristics within the lymphocyte gate are analyzed in the second aliquot. Because irrelevant monoclonal antibodies are used, none of the cells in the lymphocyte gate should be specifically labeled. Accordingly, the fluorescence markers positions are set to define "negative" and "positive" boundaries for both FL1 and FL2 and also defined the percentage of cells non-specifically stained. The information obtained from the analysis of the second aliquot is retained, as above.

A third aliquot of the blood sample then is provided from which it is desired to analyze any of the various subpopulations of cells, preferably of lymphocytes. A third monoclonal antibody which is reactive with a first subpopulation of lymphocytes is labeled with a third fluorochrome. A fourth monoclonal antibody which is specific for a second subpopulation of lymphocytes is labeled with a fourth fluorochrome. It is understood that the third fluorochrome and the fourth fluorochrome can be identical to the first and second fluorochromes previously described for use in analyzing the first aliquot of the sample and that other subpopulations of lymphocytes also may be labeled by the third and fourth monoclonal antibodies.

A mixture of the third aliquot, the third labeled monoclonal antibody and the fourth labeled monoclonal antibody is then prepared so as to cause the third monoclonal antibody to label a first lymphocyte subpopulation and the fourth monoclonal antibody to label a second lymphocyte subpopulation.

Preferably, the third sample aliquot then is analyzed by flow cytometry using forward light scatter, side light scatter and fluorescent excitation energy so as to distinguish the subpopulations of lymphocytes recognized by the third monoclonal antibody and the fourth monoclonal antibody. The third aliquot analysis is performed on the basis of the lymphocyte gate and fluorescence markers established by the first and second sample aliquot analysis.

BRIEF DESCRIPTION OF THE DRAWINGS

FIG. 1 comprises several dot plots of SSC versus FSC (A), FL2 versus FL1 (B), FL2 versus SSC (C) and FL1 versus FSC (D) for a sample of cells taken from erythrocyte lysed whole blood labeled with Anti-HLe 1 (FITC) and Anti-Leu M3 (PE) wherein X represents the SSC channel that delineates the boundary between lymphocytes (including debris) and other cells, Y represents the FSC channel that delineates the boundary between cells and debris, X' represents the FL2 channel that delineates the boundary between cells (including debris) and monocytes and Y' represents the FL1 channel that delineates the boundary between lymphocytes and cells (including debris), wherein the selection of X and Y are set so as to include the maximum number of lymphocytes while minimizing contamination from other cells or debris, and further wherein the figure comprises a dot plot of FL2 versus FL1 (E) of the cells falling within the boundaries set in (A).

The scope of the present invention will become more apparent from the following detailed description and the accompanying claims.

DETAILED DESCRIPTION

While the present invention is satisfied by embodiments in many different forms, there is shown in the drawings and will herein be described in detail a particular embodiment of the invention, with the understanding that the following description is to be considered as exemplary of the principles of the invention and is not intended to limit the scope of the invention as determined by the appended claims and their equivalent.

The present invention provides a method for identifying and enumerating cells in subpopulations of leukocytes in a population of interest in a blood sample utilizing a gate established in a flow cytometry apparatus by analysis of the entire blood sample. This gate excludes observation of cells which are not within the population of interest. For convenience of discussion, the blood sample described is lysed whole blood which contains substantially all leukocytes and the population of interest is the lymphocytes.

Figure 1A:
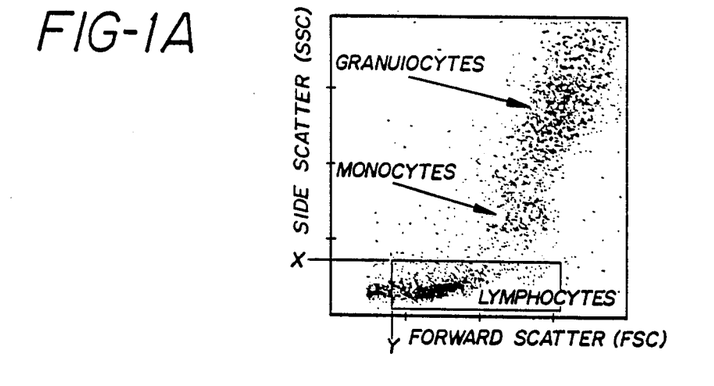
Figure 1B:
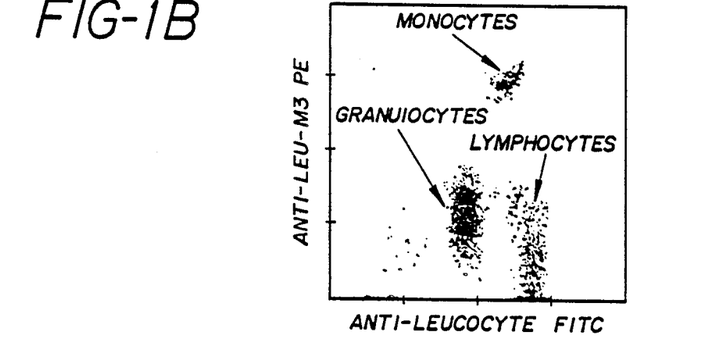
Figure 1C:
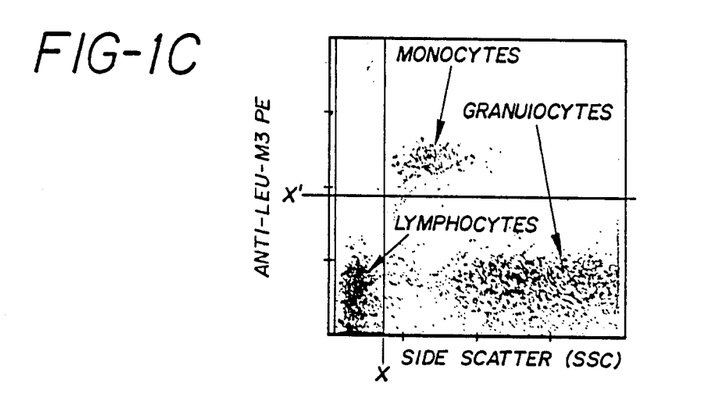
Figure 1D:
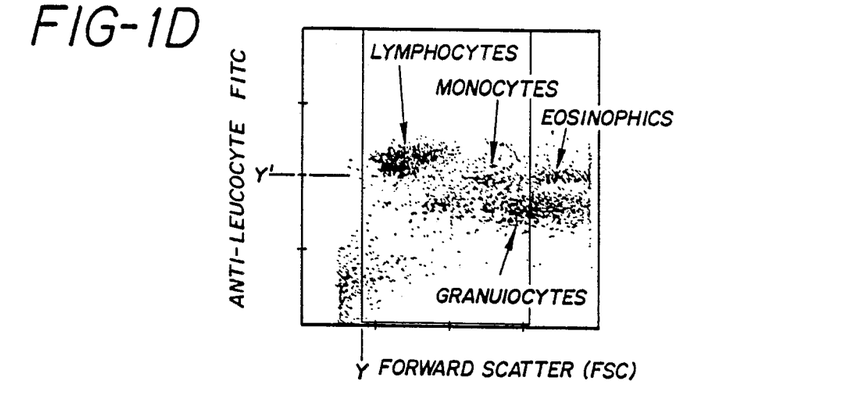
Figure 1E:
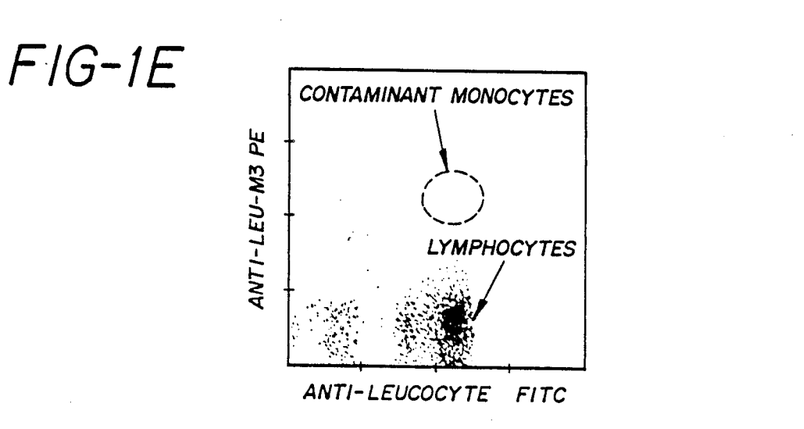
Figure 2A:
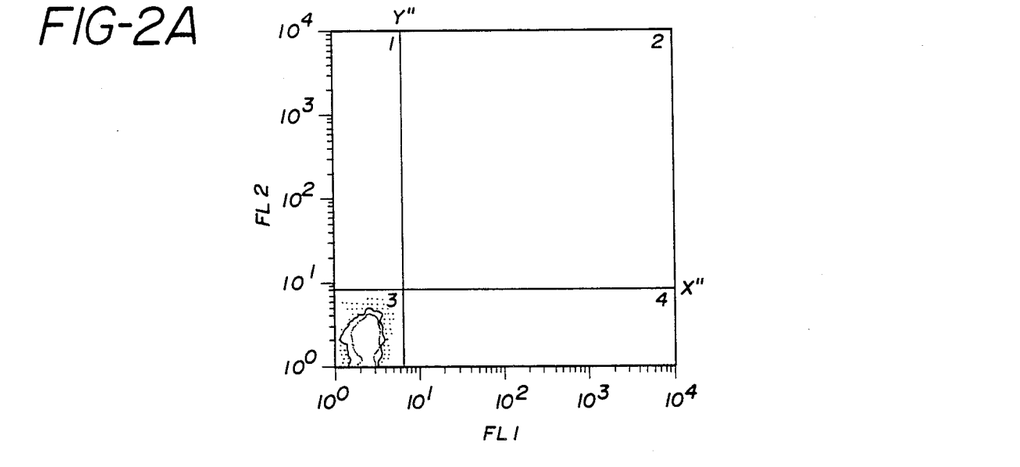
FIG. 2 is a dot plot of FL2 versus FL1 (A) and two histograms (one for each parameter, B-C respectively) for cells in the second aliquot which have been stained with irrelevant isotype control monoclonal antibodies labeled with PE and FITC and which call within the boundaries set for the lymphocyte gate in FIG. 1 wherein X" and Y" represent an upper boundary for FL2 and FL1 respectively that includes greater than 95% of all cells.
Figure 2B:
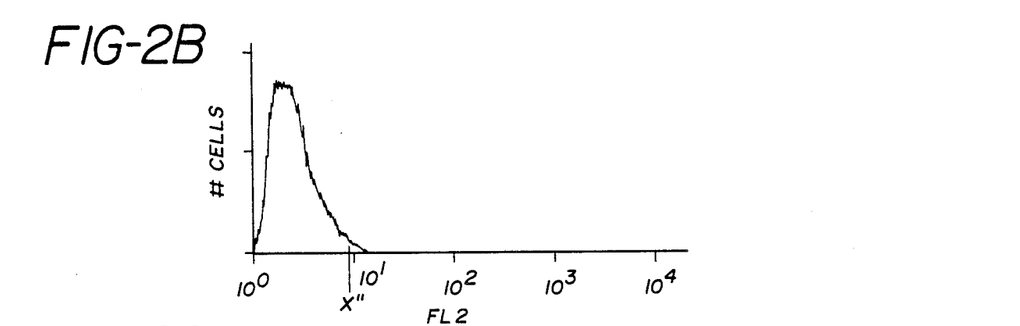
Figure 2C:
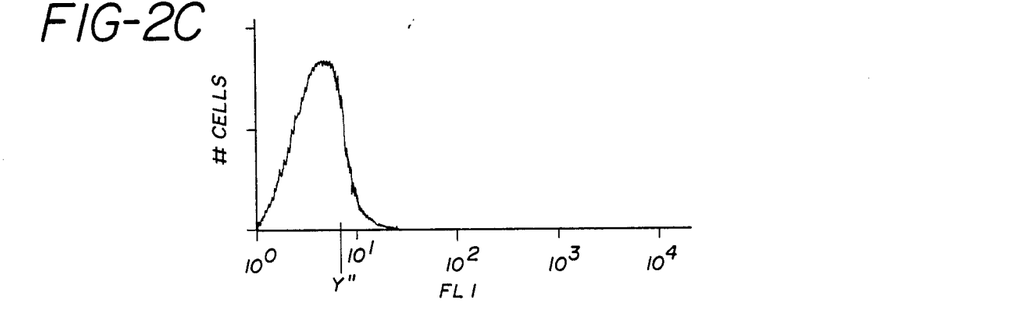
Figure 3A:
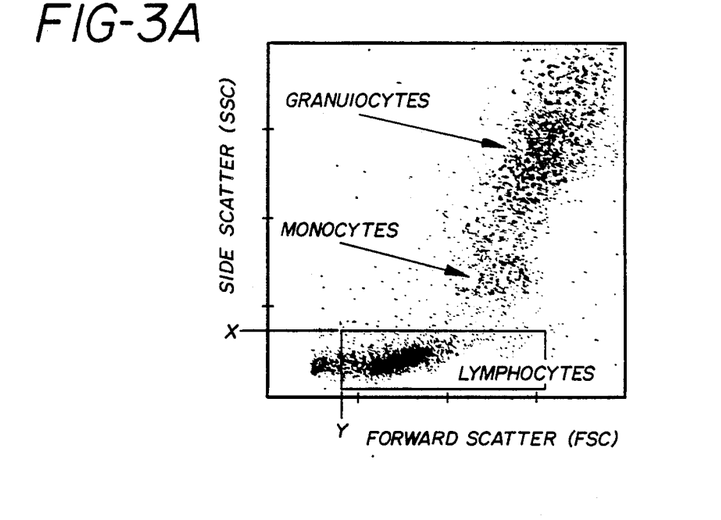
FIG. 3 comprises two dot plots of cells in the third aliquot which have been labeled with Anti-Leu 4 (FITC) and Anti-Leu 12 (PE) monoclonal antibodies wherein cells (as above) are plotted for SSC versus FSC (A) and only the cells falling within the lymphocyte gate from FIG. 1(A) are replotted for FL2 versus FL1 (B) and wherein the fluorescence markers from FIG. 2(B) are used to define positive and negative fluorescence boundaries.
Figure 3B:
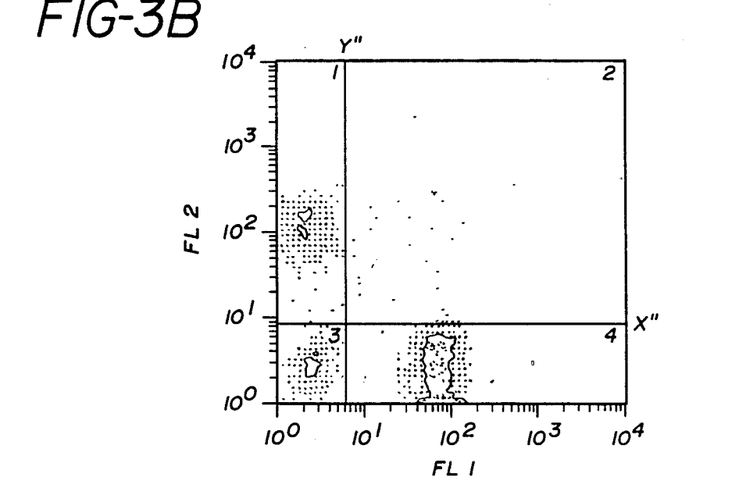

In the method as depicted in FIGS. 1-3 a first aliquot of a blood sample is provided which includes substantially all of the leukocytes. Referring to FIG. 1, a first monoclonal antibody is labeled with a first fluorochrome, which is fluorescein isothiocyanate (FITC). The first monoclonal antibody, which is Anti-HLe-1, reacts with substantially all the leukocytes in the sample. Anti-HLe-1 and all monoclonal antibodies referred to herein, unless otherwise noted, are commercially available from Becton Dickinson Immunocytometry Systems, San Jose, Calif. A second monoclonal antibody is labeled with a second fluorochrome, which is phycoerythrin (PE). The second monoclonal antibody, which is Anti-Leu-M3, reacts with substantially all of the monocytes in the aliquot. The first fluorochrome and the second fluorochrome have emission spectra which are different.

A mixture of the first aliquot, the first labeled monoclonal antibody and the second labeled monoclonal antibody is then prepared so as to cause the leukocytes to become labeled with the first monoclonal antibody and the monocytes to also become labeled with the second monoclonal antibody. It will be appreciated from FIG. 1 that each population of cells will react differentially with each of the antibodies such that the level of fluorescence emissions can be used to distinguish between cells. The first aliquot is then analyzed by flow cytometry with a FACScan™ flow cytometer (Becton Dickinson Immunocytometry Systems) using forward light scatter, side light scatter and fluorescent excitation energy so as to distinguish the lymphocyte population of the leukocytes and provide a lymphocyte gate. The parameters X and Y are selected so as to delineate the boundary between lymphocytes and other cell populations (including debris). See FIGS. 1 (C,D). Selection of the specific channel by the algorithm includes the use of X' and Y' which further distinguishes one population from another resulting in a gate that maximizes the number of lymphocytes within the gate while minimizing contamination. The information obtained from the analysis of the first aliquot is retained, preferably in a computer (e.g., a Consort 30 Data Management System, Becton Dickinson Immunocytometry Systems). The analysis of the first aliquot also provides information concerning the percentage of monocytes, granulocytes and debris within the lymphocyte gate. See FIG. 1(B).

In the preferred embodiment of the invention, a second aliquot of the blood sample is analyzed by flow cytometry to determine the fluorescence markers for the sample. See FIG. 2. To determine the fluorescence markers, the second aliquot is passed through the flow cytometer and data collected for the forward light scatter, side light scatter and fluorescent excitation parameters. The data are analyzed by applying the lymphocyte gate from the first aliquot so that only information from the cells falling within the boundaries of SSC and FSC set by the lymphocyte gate is used to determine the fluorescence markers. The boundaries for the markers again can be set by an algorithm which is calculated to include 95% of the cells on the fluorescence histograms. See FIGS. 2(B,C). The use of this second aliquot is preferred since data relative to background fluorescence (i.e., non-specific staining) can be more precisely quantified. The fluorescence marker information can be further optimized by use of two labeled irrelevant monoclonal antibodies which do not react with any leukocytes, one of which is an anti-IgG$_1$ monoclonal antibody labeled with FITC and the other of which is an anti-IgG$_2$ monoclonal antibody labeled with PE.

If a second aliquot is analyzed as in the preferred embodiment, a third aliquot of the blood sample then is provided from which it is desired to analyze any of various subpopulations of lymphocytes. If, however, the second aliquot is omitted, the "third" aliquot is used to establish the fluorescence markers as well as to analyze the various subpopulations of lymphocytes and may be defined as the second aliquot.

In a specific example of the preferred embodiment, a third monoclonal antibody which reacts with a first subpopulation of lymphocytes, such as Anti-Leu-4 (i.e., anti-CD3) which reacts with all T-cells, is labeled with FITC, as shown in FIG. 3. A fourth monoclonal antibody which reacts with a second subpopulation of lymphocytes, such as Anti-Leu 12 (i.e., anti-CD19) which is specific for B-cells, is labeled with another fluorochrome, such as PE, as shown in FIG. 1.

A mixture of the third aliquot, the third labeled monoclonal antibody and the fourth labeled monoclonal antibody then is prepared so as to cause the third monoclonal antibody to label a first lymphocyte subpopulation (T-cells) and the fourth monoclonal antibody to label a second lymphocyte subpopulation (B-cells). The third aliquot then is analyzed by flow cytometry using forward light scatter, side light scatter and fluorescence excitation energy so as to distinguish the subpopulations of lymphocytes recognized by the third monoclonal antibody and the fourth monoclonal antibody. The third aliquot analysis is performed on the basis of a lymphocyte gate established by the first aliquot analysis and the fluorescence markers established by the second aliquot analysis.

In the context of the present invention, monoclonal antibodies are used as marking agents. A tagging agent comprises a light emitting agent which alone or in combination with a marking agent can label a structure(s) in or on a cell. The tagging agents for marking the various cell populations in the method of the invention are preferably monoclonal antibodies conjugated to a suitable fluorochrome. Other suitable tagging agents are lectins, nucleic acid dyes, such as propidium iodide, and membrane potential dyes, such as cyanine dyes. Some tagging agents, such as monoclonal antibodies, react with antigenic sites on the surface of the cells. Other tagging agents, such as nucleic acid dyes and membrane potential dyes are absorbed by a specific cellular component so as to mark the subpopulation or population of cells of interest.

Fluorescence emission of certain tagging agents which do not spontaneously emit detectable light (such as monoclonal antibodies) may be obtained by coupling a marking agent to a suitable emitting agent, such as a fluorochrome. Some tagging agents (such as nucleic acid dyes and membrane potential dyes) have fluorescent properties and spontaneously emit detectable light upon optical stimulation. For such cases, a coupled marking agent is not required. The emitting agents for use with non-spontaneously emitting marking agents are preferably two or more fluorochromes which have emission spectra with sufficient wave length separation to permit simultaneous detection of two or more colors. In general, the fluorochromes should emit fluorescence in the range of from about 10 to about 300 nm above the excitation wave length. One particularly suitable pair of marking agents has been found to be phycoerythrin, (PE), a phycobiliprotein which emits fluorescence at 570 nm and fluorescein isothiocyanate (FITC) which emits fluorescence at a wave length of 530nm. Both PE and FITC are excited at the 488 nm wavelength. Three or more suitable tagging agents can be used for analysis of aliquots if they have suitably distinct emission properties or are tagged with emitting agents having suitably distinct emission properties. One suitable group of three fluorochromes for coupling to antibodies are phycoerythrin, fluorescein isothiocyanate, and a phycoerythrin-texas red conjugate which emits fluorescence at 615 nm. One or more of these marking agents may be used in combination with a nucleic acid dye, such as propidium iodide.

If whole blood is used, the incubated aliquot is passed through a flow cytometry apparatus at a white blood cell flow rate that is substantially equivalent to the white blood cell flow rate that is normally used for samples wherein the red blood cells are removed or lysed. In general, flow rates of from about 20 to about 1000 white blood cells/sec. are suitable. Preferably, the aliquot is passed through the flow cytometry apparatus following lysis or separation of the white blood cells from the red blood cells by method known to those skilled in the art (e.g., FACS TM Lysing Solution, Becton Dickinson Immunocytometry Systems). It should be understood, however, that the principles of the present invention are equally suitable for the analysis of blood cell fractions which include the white blood cells which are provided by lysis of red blood cells or separation of specific subpopulations of blood cells from the sample under investigation, as well as from whole blood cell preparations including red blood cells and white blood cells.

The subpopulations of lymphocytes which can be distinguished by the method of the invention include T-cells, helper T-cells, inducer T-cells, suppressor T-cells, cytotoxic T-cells, T-cells in maturation/activation stages, B-cells, B-cells in maturation/activation stages, NK/LGL cells and NK/LGL cells in maturation/activation stages. Of course, the method of this invention can be used to distinguish and compare two or more sets of the subpopulations enumerated hereinabove.

By suitable selection of the second monoclonal antibody and second fluorochrome, populations of cells other than lymphocytes, such as granulocytes and monocytes, can be examined. Like the lymphocyte population, within each of the other populations, other subpopulations can be examined. For example, if the population is granulocytes, the subpopulations can be neutrophils, eosinophils, basophils, maturation stage granulocytes and combinations thereof.

In particular, a preferred population of cells is lymphocytes and the following pairs of lymphocyte subpopulations:
(1) T-cells and B-cells;
(2) CD4 bearing cells and cells expressing the Leu 8 antigen;
(3) T-cells and activation antigens expressed by T-cells;
(4) CD4 bearing cells and CD8 bearing cells; and
(5) CD8 bearing cells and cells expressing the Leu 7 antigen (i.e., CD57).

The "CD" designation for antigens is the International standard for leukocyte antigens for which monoclonal antibodies have been developed. The "Leu" designation for antigens is the Becton Dickinson Immunocytometry Systems system for antigens for which monoclonal antibodies have been developed and commercialized.

It is understood that the present invention is useful in many types of flow cytometry devices which measure light scatter, particle or cell volume, fluorescence or any other optical parameters for the identification or quantification of subpopulations of particles in a sample. For example, the elements of a suitable flow cytometry apparatus are included in a FACScan TM flow cytometer. The FACScan TM flow cytometer analyzes cell populations on the basis of light scatter and fluorescence in a wide variety of research and laboratory applications. Other details of a cell analysis and sorting apparatus useful in conjunction with the present invention are described in U.S. Pat. No. 3,826,364.

In accordance with one embodiment of the invention, a computer (e.g., Consort 30) is provided to retain the results of the analysis of the first and second aliquots of the blood sample to provide the lymphocyte gate and fluorescence markers which are used in the analysis of the subsequent aliquots of the blood sample. When two labeled antibodies are used, a two dimensional plot of fluorescence properties of the cell populations is generated. When three labeled antibodies are used a representational three dimensional plot can be generated or a series of two dimensional plots can be generated showing subpopulations of cells in groups of two.

The present invention is also directed to providing a kit for use in the practice of the method of the invention. In its simplest form the kit includes a vial or other suitable container filled with a mixture of a first monoclonal antibody coupled to a first fluorochrome and a second monoclonal antibody coupled to a second fluorochrome. The first monoclonal antibody is specific for substantially all leukocytes and the second monoclonal antibody is specific for substantially all monocytes. The first and second fluorochromes have different light emission properties, as described hereinabove.

The kit can also contain one or more additional vials containing one or mixtures of one or more monoclonal antibodies coupled to suitable fluorochromes. In each additional vial, there is most commonly a set of two monoclonal antibodies reactive with particular subpopulations of lymphocytes.

The following examples further illustrate various features of the invention but are intended to in no way limit the scope of the invention for detecting, distinguishing and/or quantifying subpopulations of lymphocytes.

EXAMPLE 1

In this example, as exemplified in FIGS. 4–9, two components or subsets of lymphocytes, (i.e., T-cells and B-cells) were determined as a percentage of total lymphocytes from a human blood source.

For the first analysis an aliquot of 0.05 cc (50 microliters) of suspended peripheral blood cells were added to 0.02 cc of a mixture of a first monoclonal antibody Anti-HLe-1 (i.e., anti-CD45) conjugated to fluorescein isothiocyanate, and a second monoclonal antibody Anti-Leu-M3 (i.e., anti-CD14) conjugated to phycoerythrin. The aliquot was maintained at room temperature at the time of addition and thereafter for one-half hour. After one-half hour of incubation, a further addition of 3 ml of a red cell lysing solution (e.g., FACS TM Lysing Solution) was made and the sample was mixed and held for 10 minutes.

The first aliquot was passed through a flow cytometry apparatus (e.g., FACScan TM ), and was analyzed to provide forward light scatter, side light scatter, fluorescence one channel data and fluorescence two channel data. A representation of the results obtained from analysis of the first aliquot is shown in FIG. 4 and FIG. 5.

The data generated by analysis of the first aliquot was retained in a computer (e.g., Consort 30) having an algorithm (as described above) designed to analyze the data using all four parameters and provide a lymphocyte gate around the group of lymphocyte cells.

Figure 4:
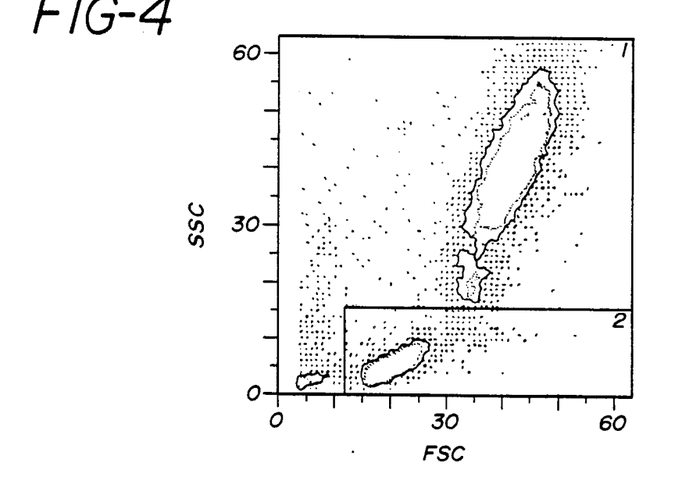
FIG. 4 and FIG. 5 represent flow cytometry results obtained from analysis of a first aliquot of a blood sample.
Figure 5:
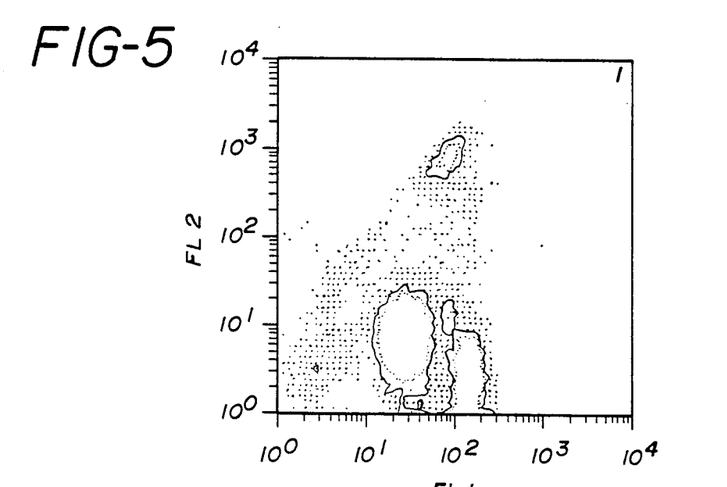

As shown in FIG. 4, the results of this first analysis using forward light scatter and side light scatter are isolation of four populations of cells. One population represents monocytes, one population represents granulocytes, one population represents debris and the other population are the cells of interest (i.e., the lymphocytes). As shown in FIG. 5, the analysis of the two colors, phycoerythrin and fluorescein isothiocyanate, also provide four populations of cells. As shown in FIG. 1, the four populations are the same as the four populations generated by analysis of forward light scatter and side light scatter. The algorithm used with the computer is designed to compare the data generated by light scatter, as shown in FIG. 4 and the data generated by fluorescence analysis, as shown in FIG. 5 and to differentiate those cells which should be included within the lymphocyte gate. The objective is to set a gate around the lymphocyte population using the physical parameters, forward and side light scatter. The physical properties (FIG. 4) and the fluorescence (FIG. 5) properties are used to determine the location of the lymphocytes on the forward light scatter vs. side light scatter plot. Any interference from debris, monocytes or granulocytes that exist is quantified and reported but cannot removed from consideration. Since the physical properties for the sample will remain constant for all aliquots of the sample, the lymphocyte gate is applied and subsequent analysis of a second or further aliquots of the sample need only contain the fluorescent plot for the monoclonal antibodies used for the lymphocyte subsets of interest.

As shown in FIG. 2 and using the preferred embodiment, a second aliquot containing isotype control monoclonal antibody reagents is prepared. The $IgG_1$ monoclonal antibody is conjugated to fluorescein isothiocyanate and the $IgG_2$ monoclonal antibody is conjugated to phycoerythrin.

Figure 6:
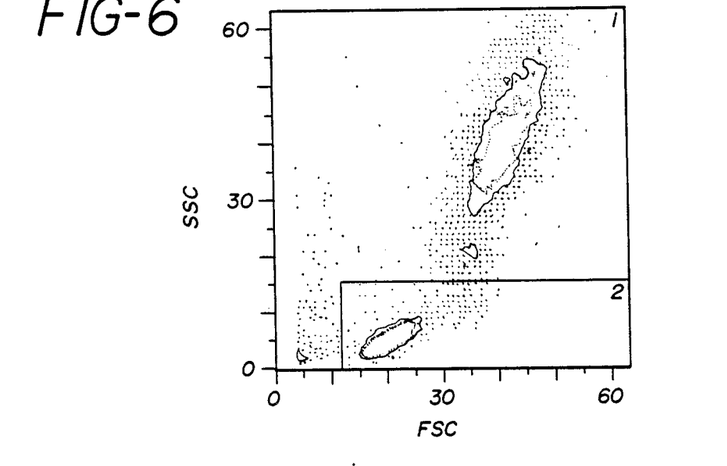
FIG. 6 and FIG. 7 represent flow cytometry results obtained from analysis of a second aliquot of the same sample.
Figure 7:
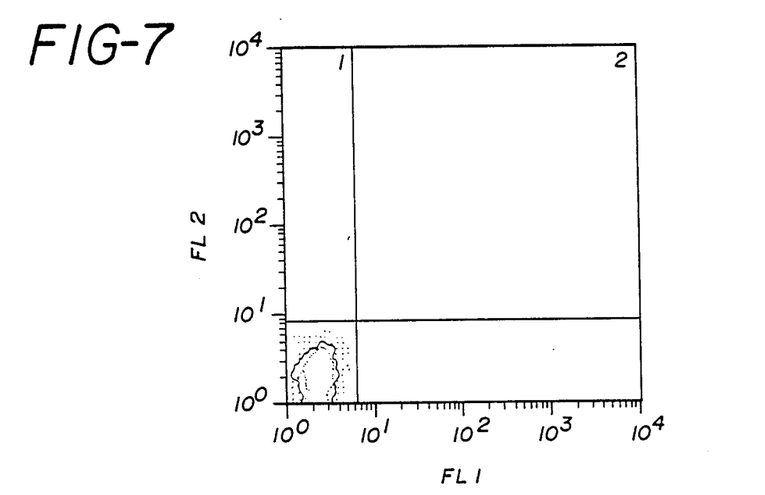

FIGS. 6 and 7 depict the four parameter representation of the second aliquot after incubation with the $IgG_1$, and $IgG_2$ antibodies and passage through a flow cytometry apparatus. FIG. 6 shows the lymphocyte gate set by the data retained from the analysis of the first aliquot and FIG. 7 shows the fluorescence markers that are calculated using the gated fluorescence data for this sample. Non-specific staining is the percent of gated events which fall in the upper left, upper right, and lower right quadrants. The quadrant counts are corrected for interference from monocytes, granulocytes or debris that was quantified in the first sample aliquot.

As shown in FIG. 2, a third aliquot containing T-cell and B-cell monoclonal antibody reagents is prepared. The T-cell monoclonal antibody reagent is Anti-Leu 4 conjugated to fluorescein isothiocyanate and the B-cell monoclonal antibody reagent is Anti-Leu-12 conjugated to phycoerythrin.

Figure 8:
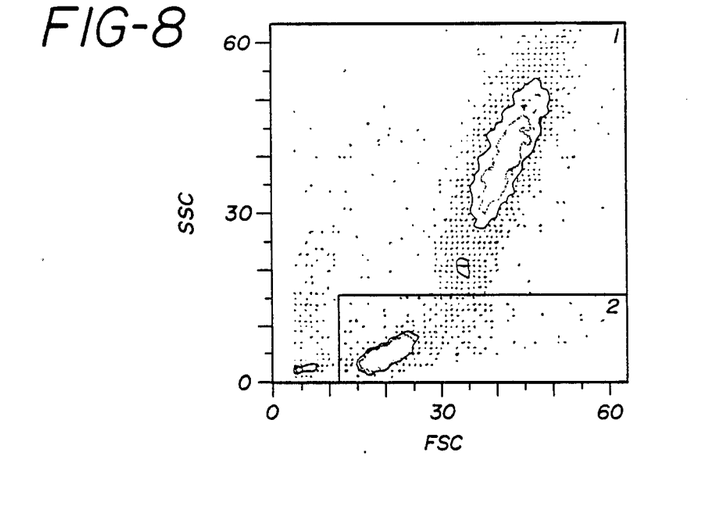
FIG. 8 and FIG. 9 represent flow cytometry analysis of a third aliquot of the same sample.
Figure 9:
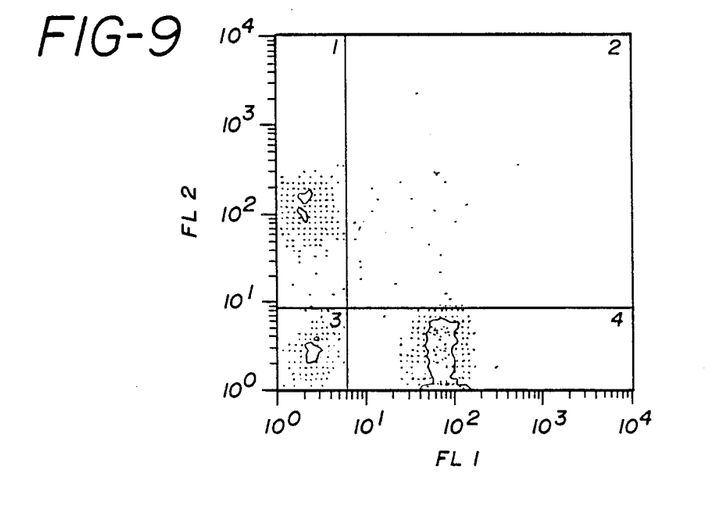

FIGS. 8 and 9 depict the four parameter representation of the third aliquot after incubation with the Leu-12 and Leu-4 monoclonal antibodies and passage through a flow cytometry apparatus. FIG. 8 shows the lymphocyte gate set by the data retained from the analysis of the first aliquot and FIG. 9 shows the fluorescence markers set by the second aliquot analysis and gated fluorescence data for the third aliquot T-cells are in the lower right quadrant of FIG. 9, B-cells are in the upper left quadrant and T+/B+ cells are in the upper right quadrant. The quadrant counts are corrected for interference from monocytes, granulocytes or debris that was quantified in the first sample aliquot.

EXAMPLE 2

A blood sample was again analyzed for T-cells and B-cells as a percentage of total lymphocytes in accordance with the procedure of Example 1.

In this example, the second aliquot analysis was omitted. The fluorescence markers were calculated from the third aliquot wherein Anti-Leu-12 and Anti-Leu-4 were used. Other suitable combinations of monoclonal antibodies useful in establishing fluorescence markers include Anti-Leu-3 and Anti-Leu-2.

The present invention provides a method for analysis of subpopulations of lymphocytes without risk of operator error through establishment of an improper lymphocyte gate for the flow cytometry apparatus.

What is claimed:

1. In a method of identifying and enumerating two or more subpopulations of a population of cells of interest in a whole blood sample by means of flow cytometry, wherein the sample has been split into three aliquots, wherein the first aliquot is labeled with a first fluorescently labeled monoclonal antibody and a second fluorescently labeled monoclonal antibody that react differentially with all of populations of cells in such a manner as to separate the populations from one another when both antibodies are used, the second aliquot is labeled with a first fluorescently labeled irrelevant control and a second fluorescently labeled irrelevant control, and the third aliquot is labeled with a third fluorescently labeled monoclonal antibody and a fourth fluorescently labeled monoclonal antibody that are different from the first and second monoclonal antibodies and react differentially with the cells of the subpopulations of interest, and wherein the fluorescent label on the first antibody, first control and third antibody are the same and the fluorescent label on the second antibody, second control and fourth antibody are the same but which has an emission spectra different from the other fluorescent label, the improvement comprising the steps of:
   (a) establishing a cell population gate that will contain the maximum number of all cells in the population of interest with a minimum level of contamination from other cell populations by analyzing the first aliquot and selecting the gate based upon an analysis SSC and FL2 to set the SSC boundary and FSC and FL1 to set the FSC boundary and calculating the percentage of contamination of other populations of cells within the gate;
   (b) establishing fluorescence markers for each of the fluorescence labels used by analyzing the second aliquot applying the gate from step (a) and selecting the markers based upon fluorescence emissions and calculating the percentage of non-specific staining in the sample; and
   (c) analyzing the third aliquot using the gate and percent contamination from step (a) and the fluorescence markers and percent non-specific staining from step (b) to identify and enumerate cells in each subpopulation.

2. The method of claim 1 wherein the cell population gate of step (a) includes greater than 98% of all cells in the population of interest.

3. A method in accordance with claim 1 wherein erythrocytes are removed from the whole blood sample.

4. A method in accordance with claim 1 wherein said population of interest comprises lymphocytes.

5. A method in accordance with claim 1 wherein said first monoclonal antibody reacts with substantially all leukocytes and said second monoclonal antibody reacts with substantially all monocytes.

6. A method in accordance with claim 4 wherein said third monoclonal antibody reacts with substantially all T-cells and said fourth monoclonal antibody reacts with substantially all B-cells.

7. A method in accordance with claim 5 wherein said third monoclonal antibody reacts with substantially all T-cells and said fourth monoclonal antibody reacts with substantially all B-cells.

8. A method in accordance with claim 4 wherein said third monoclonal antibody reacts with substantially all T-cells and said fourth monoclonal antibody reacts with at least one activation antigen expressed by T-cells.

9. A method in accordance with claim 5 wherein said third monoclonal antibody reacts with substantially all T-cells and said fourth monoclonal antibody reacts with at least one activation antigen expressed by T-cells.

10. A method in accordance with claim 4 wherein said third monoclonal antibody reacts with substantially all CD4 bearing cells and said fourth monoclonal antibody reacts with substantially all cells expressing the Leu 8 antigen.

11. A method in accordance with claim 5 wherein said third monoclonal antibody reacts with substantially all CD4 bearing cells and said fourth monoclonal antibody reacts with substantially all cells expressing the Leu 8 antigen.

12. A method in accordance with claim 4 wherein said third monoclonal antibody reacts with substantially all CD4 bearing cells and said fourth monoclonal antibody reacts with substantially all CD8 bearing cells.

13. A method in accordance with claim 5 wherein said third monoclonal antibody reacts with substantially all CD4 bearing cells and said fourth monoclonal antibody reacts with substantially all CD8 bearing cells.

14. A method in accordance with claim 4 wherein said third monoclonal antibody reacts with substantially all CD8 bearing cells and said fourth monoclonal antibody reacts with substantially all cells expressing the Leu 7 antigen.

15. A method in accordance with claim 5 wherein said third monoclonal antibody reacts with substantially all CD8 bearing cells and said fourth monoclonal antibody reacts with substantially all cells expressing the Leu 7 antigen.

16. A method in accordance with claim 1 wherein said sample is a peripheral blood sample.

17. A method in accordance with claim 1 wherein the population of interest comprises monocytes.

18. A method in accordance with claim 1 wherein the population of interest comprises granulocytes.

19. In a method of identifying and enumerating two or more subpopulations of lymphocytes in a whole blood sample, from which the erythrocytes have been removed, by means of flow cytometry, wherein the sample has been split into three aliquots, wherein the first aliquot is labeled with a first fluorescently labeled monoclonal antibody that reacts with substantially all leukocytes and a second fluorescently labeled monoclonal antibody that reacts with substantially all monocytes, the second aliquot is labeled with a first fluorescently labeled irrelevant control and a second fluorescently labeled irrelevant control, and the third aliquot is labeled with a third fluorescently labeled monoclonal antibody and a fourth fluorescently labeled monoclonal antibody that are different from the first and second monoclonal antibodies and react differentially with the subpopulations of lymphocytes, and wherein the fluorescent label on the first antibody, first control and third antibody are the same and the fluorescent label on the second antibody, second control and fourth antibody are the same but which has an emission spectra different from the other fluorescent label, the improvement comprising the steps of:

(a) establishing a lymphocyte gate that will contain the maximum number of all lymphocytes with a minimum level of contamination from other cell populations and debris by analyzing the first aliquot and selecting the gate based upon an analysis of SSC and FL2 to set SSC limit and analysis of FSC and FL1 to set FSC limit and calculating the percentage of contamination of other populations of cells within the gate;

(b) establishing fluorescence markers for each of the fluorescence labels used by analyzing the second aliquot applying the gate from step (a) and selecting the markers based upon fluorescence emissions and calculating the percentage of non-specific staining in the sample, and (c) analyzing the third aliquot using the gate and percent contamination from step (a) and the fluorescence markers and percent non-specific staining from step (b) to identify and enumerate cells in each subpopulation.

20. The method of claim 19 wherein the lymphocyte gate of step (a) includes greater than 98% of all lymphocytes.

21. A method in accordance with claim 19 wherein said third monoclonal antibody reacts with substantially all T-cells and said fourth monoclonal antibody reacts with substantially all B-cells.

22. A method in accordance with claim 19 wherein said third monoclonal antibody reacts with substantially all T-cells and said fourth monoclonal antibody reacts with at least one activation antigen expressed by T-cells.

23. A method in accordance with claim 19 wherein said third monoclonal antibody reacts with substantially all CD4 bearing cells and said fourth monoclonal antibody reacts with substantially all cells expressing the Leu 8 antigen.

24. A method in accordance with claim 19 wherein said third monoclonal antibody reacts with substantially all CD4 bearing cells and said fourth monoclonal antibody reacts with substantially all CD8 bearing cells.

25. A method in accordance with claim 19 wherein said third monoclonal antibody reacts with substantially all CD8 bearing cells and said fourth monoclonal antibody reacts with substantially all cells expressing the Leu 7 antigen.

* * * * *